United States Patent
Park et al.

(10) Patent No.: US 7,403,891 B2
(45) Date of Patent: Jul. 22, 2008

(54) APPARATUS AND METHOD FOR RECOGNIZING BIOLOGICAL NAMED ENTITY FROM BIOLOGICAL LITERATURE BASED ON UMLS

(75) Inventors: Soo Jun Park, Seoul (KR); Tae Hyun Kim, Taejon (KR); Hyun Sook Lee, Taejon (KR); Hyun Chul Jang, Taejon (KR); Seon Hee Park, Taejon (KR)

(73) Assignee: Electronics and Telecommunications Research Institute, Taejon (KR)

( * ) Notice: Subject to any disclaimer, the term of this patent is extended or adjusted under 35 U.S.C. 154(b) by 880 days.

(21) Appl. No.: 10/777,072

(22) Filed: Feb. 13, 2004

(65) Prior Publication Data

US 2005/0091081 A1      Apr. 28, 2005

(30) Foreign Application Priority Data

Oct. 23, 2003    (KR)    .................. 10-2003-0074429

(51) Int. Cl.
*G06F 17/27* (2006.01)
*G06F 17/21* (2006.01)
*G06F 7/00* (2006.01)
*G06F 17/30* (2006.01)
*G10L 15/00* (2006.01)

(52) U.S. Cl. .................... 704/10; 704/9; 704/238; 704/239; 707/3; 707/102

(58) Field of Classification Search .............. 704/9, 704/10, 238, 239; 707/3, 102
See application file for complete search history.

(56) References Cited

U.S. PATENT DOCUMENTS 5,819,265 A * 10/1998 Ravin et al. .................. 707/5
6,311,152 B1 * 10/2001 Bai et al. ..................... 704/9
6,584,470 B2 * 6/2003 Veale ......................... 707/102

OTHER PUBLICATIONS

Johnson, S.B., "A Semantic Lexicon for Medical Langauge Processing", JAMIA, vol. 6, No. 3, May/Jun. 1999, pp. 205-218.*
McCray, A et al, "Aggregating UMLS semantic Types for Reducing Conceptual Complexity", In Proceedings of Medinfo, 2001, pp. 216-220.*
Friedman, C et al, "Evaluating the UMLS as a source ofr Lexical Knowledge for Medical Language Processing", In proceedings AMIA 2001, pp. 189-193.*
Pustejovsky, J. et al, "Rerendering Semantic Ontologies: Automatic Extensions to UMLS through Corpus Analytics", In Proceedings of REC 2002, Workshop on Ontologies and Lexical Knowledge Bases.*

(Continued)

*Primary Examiner*—Richemond Dorvil
*Assistant Examiner*—Dorothy S Siedler
(74) *Attorney, Agent, or Firm*—Lowe Hauptman Ham & Berner LLP

(57) ABSTRACT

The present invention relates to an apparatus and method for recognizing biological named entity from biological literature based on united medical language system (UMLS). The apparatus and the method receives metathesaurus from the UMLS, constructs a concept name database, a single name database and a category keyterm database, which are language resources to be used recognize a named entity, receives each concept name stored in the concept name database, extracts features of each of the concept names by using data stored in the single name database and the category keyterm database, constructs a rule database by creating rules used to recognize the named entity and filtering the rules by using the extracted features, receives a biological literature, extracts nouns and noun phrases that are candidate named entities, applies the rules stored in the rule database to the nouns and the noun phrases, and recognizes the named entities. In the present invention, the biological named entities can be effectively extracted which can be used as important information individual in input literature.

9 Claims, 6 Drawing Sheets

OTHER PUBLICATIONS

McCray, A et al, "Evaluating UMLS Strings for NAtural Language Processing", In Proceedings of AMIA 2001, pp. 448-452.*

Kirsch, H et al, "Distributed Modules for Text Annotation and IE applied to the Biomdeical Domain", COLING Workshop on Natural Language Processing in Biomedicine and its Application, 2004, pp. 50-53.*

Gaizauskas R. et al, "Term Recognition and CLassfication in Biological Science Journal Articles", In 2nd National Conference on Natural Language Processing, 2000.*

Irena Spasic, et al.; "*Using Domain-Specific Verbs for Term Classification*"; Proceedings of the ACL 2003 Workshop on Natural Language Processing in Biomedicine; pp. 17-24.

David A. Campbell, et al.; "*A Technique for Semantic Classification of Unknown Words Using UMLS Resources*".

* cited by examiner

FIG. 3

MIRCON

| CUI | LAT | TS | LUT | STT | SUI | STR | LRL |
|---|---|---|---|---|---|---|---|
| Unique identifier for concept | Language of Tem | Term status | Unique identifier for term | String type | Unique identifier for string | String | Least Restriction Level |

Sample Records

C0002871|ENG|P|L0002781|PF|S0013742|Anemia|0|
C0002871|ENG|P|L0002781|VP|S0013787|Anemias|0|
C0002871|ENG|P|L0002781|VC|S00352787|ANEMIA|0|
C0002871|ENG|P|L0002781|VC|S0414880|anemia|0|
C0002871|ENG|P|L0002781|VO|S0470197|Anemia,NOS|3|
C0002871|ENG|S|L0280031|PF|S0803242|Anaemia|3

Mapping

| CUI | TUI | STY |
|---|---|---|
| Unique identifier for concept | Unique identifier of Semantic type | Semantic type. The valid values are defined in the Semantic Network |

Sample Records

C0002871 T047 Disease or Syndrome

MRSTY

— Condition

FIG. 4

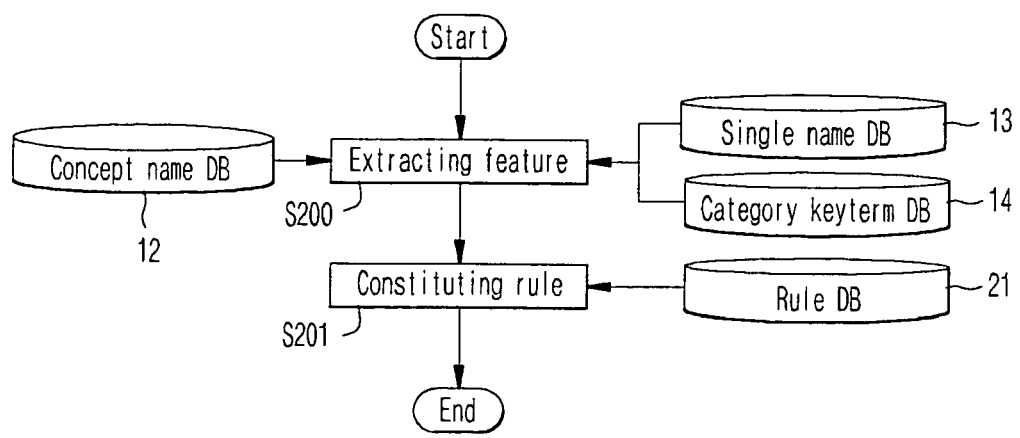

| Feature | Meaning |
|---|---|
| Single name | Word used independently and representing named entry |
| Category keyterm | Word used frequently in a particular category |
| Capital letter expression | Characteristic of structure of capital and small letters of a string constituting a token |
| Alphanumeric | Token including a number |
| Preposition and conjunction | Preposition and conjunction |
| Special character | Special character |
| Miscellanies | The other cases |

(b)

| Subtype | Example |
|---|---|
| START | Abstract |
| END | abstractA |
| ALL | ABCDE |
| MIXED | AbcDE, abAcde |
| ROMNUM | I, II, III, IV ···· |

(c)

| Subtype | Example |
|---|---|
| ONLY | 1234 |
| YEAR | 1900~2999 |
| UNIT | 10bp |
| GREEK | Ialpha, alpha10 |
| OTHER | 10abc, abc10, ab10cd |

(d) about, above, across, affeward, against, al, along, alongside, alo, amid, among, an, and, any, apart, around, as, at athwart, bar, before, behind, below, beneath, beside, besides, between, beynd, but, by, concerning, considering, despite, down, downward, during, either, et, etc, except, for forward, from, if, in, including, inside, into, inward, like, many, minus, more, much, near, neither, next, nor, nos, not, of, off, on, only, onto, onward, apposite, or, other, out, outside, outward, over, past, pending, per, plus, respecting, save, since, some, sp, such, that, the, through, throughout, till, to, too, toward, under, undemealh, until, unto, up, upon, upward, versus, via, well, whether, with, within, without (e) TAB, LF, VT, FF, CR, SPACE
!"#$%'()+,-./:;<>?@[\]^_'{|}~

(f)

| Subtype | Example |
|---|---|
| UPA | A |
| LOWA | a |
| ALPHA | b-z, B-Z |
| OTHER | The case of belonging to none of the preceding features |

```
RULE:=TOKEN (TOKEN)*
TOKEN:=FEATNUM/TYPENUM,(TYPENUM)*
FEATNUM:=One of the{1,2,3,4,5,6,7,12,13,23,123}
    /*  1=Single name, 2=Category keyterm, 3=Capital-letter expression    */
    /*  4=Alphanumeric, 5=Preposition and conjunction, 6=Special character, 7=Miscellanies    */
    /*  12,13,23,and 123 are the combinations of the feature 1,2,and 3.    */
TYPENUM:= A Number that represents each of the feature's subtype.
```

APPARATUS AND METHOD FOR RECOGNIZING BIOLOGICAL NAMED ENTITY FROM BIOLOGICAL LITERATURE BASED ON UMLS

BACKGROUND OF THE INVENTION

1. Field of the Invention

The present invention relates to an apparatus and method for recognizing biological named entity from biological literature based on united medical language system (UMLS), in which the biological named entity is recognized and grouped.

2. Description of the Related Art

As the volume of biological literature is increased by active study on biology, also increased are demands for extraction of information from the literature at high quality. A protein name, a gene name, and a name of an element of laboratory organism or living organism constitute the core of information in the biological literature that describes results of important biological studies. Accordingly, in order to extract information from the biological literature, names of the biological entity should be exactly recognized and classified first. The information extraction is performed on the literature so as to find information subjects, relation between the information subjects, and information flow of the information subject. Accordingly, even in case of extracting information from the biological literature, the biological named entities that are information subjects in the literature should be first recognized. Generally, as the method of recognizing the biological named entity, there is a rule-based method in which an expert who has biological knowledge creates various language resources and rules on an limited object domain and the named entity is recognized using the created various language resources and rules. There is also a statistic-based method in which a large amount of biological literature learning corpus is constructed and a machine learning algorithm is applied to recognize the named entity. The former method costs much in creation of language resources and rules and the latter method costs much in construction of the biological literature learning corpus.

In the prior art, the technology in which new names are recognized and extracted is registered as U.S. Pat. No. 5,819,265 "processing names in a text" on Oct. 6, 1998. However, the preceding patent does not disclose "the process of the biological literature based on UMLS" and also, the system according to the preceding patent may work erroneously if names in which names or spells appeared in the literature occasionally are similar but meanings thereof are different would be appeared.

In the other prior arts, David A. Campbell and Stephen B. Johnson reported "A Technique for Semantic Classification of Unknown Works Using UMLS Resources" in Proceedings of American Medical Informatics Association Symposium, pp 716-720 on November, 1999, and Irena Spasic, Coran Nenadic and Sophia Ananiadou reported "Using Domain Specific Verbs for Term Classification" in Proceedings of the ACL 2003 Workshop on Natural Language Processing in Biomedicine, pp 17-24 on July, 2003. In the method for recognizing the biological named entity, which is disclosed in the prior articles, UMLS and corpus should be simultaneously used and pattern rules are limited to a specific form so that it is limited to recognize the newly generated various named entities.

SUMMARY OF THE INVENTION

Accordingly, the present invention is directed to an apparatus and method for recognizing biological named entity from biological literature based on UMLS that substantially obviates one or more problems due to limitations and disadvantages of the related art.

It is an object of the present invention to provide an apparatus and method, in which a rule for named entity recognition is constituted using various features reflecting the property of the biological named entity and biological terminology resources called UMLS, and the biological named entity is recognized from the biological literature by using the rule.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, an apparatus for recognizing a biological named entity from biological literature based on united medical language system (UMLS), comprises: a resource construction unit for receiving metathesaurus from the UMLS and constructing a concept name database, a single name database and a category keyterm database, which are language resources to be used to recognize biological named entities; a rule collection unit for receiving each concept name stored in the concept name database, extracting a feature of each of the concept names by using data stored in the single name database and the category keyterm database, and constructing a rule database by creating rules used to recognize the named entity and filtering the rules by using the extracted feature; and a named entity recognition unit for receiving a biological literature, extracting nouns and noun phrases that are candidate named entities, applying the rule stored in the rule database to the nouns and the noun phrases, and recognizing the named entities.

In another aspect of the present invention, a method for recognizing biological named entities from biological literature based on UMLS, comprises the steps of: (a) receiving metathesaurus from the UMLS, extracting concept names, single names and category keyterms, which are language resources to be used to recognize biological named entities, and constructing a concept name database, a single name database and a category keyterm database; (b) extracting a feature of the concept name by using the language resources stored in each of the databases, constituting a rule for the extracted feature, storing the constituted rule in a rule database; and (c) receiving a literature, extracting a feature of a candidate named entity, creating a rule used to determine the candidate named entity by combining the extracted feature, comparing the created rule with the rule stored in the rule database, and determining a final semantic category by using a result of comparison.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings:

FIG. 3 illustrates a mapping relation between MRCON table and MRSTY table used to divide concept names according to semantic category in a method for recognizing biological named entity according to an embodiment of the present invention;

FIG. 4 illustrates a rule collection step in a method for recognizing biological named entity according to an embodiment of the present invention;

FIGS. 5A through 5F illustrate features defined to reflect property of a biological named entity in a method for recognizing biological named entity according to an embodiment of the present invention;

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

An apparatus and a method for recognizing biological named entity according to an embodiment of the present invention will be described referring to the accompanying drawings.

Figure 1:
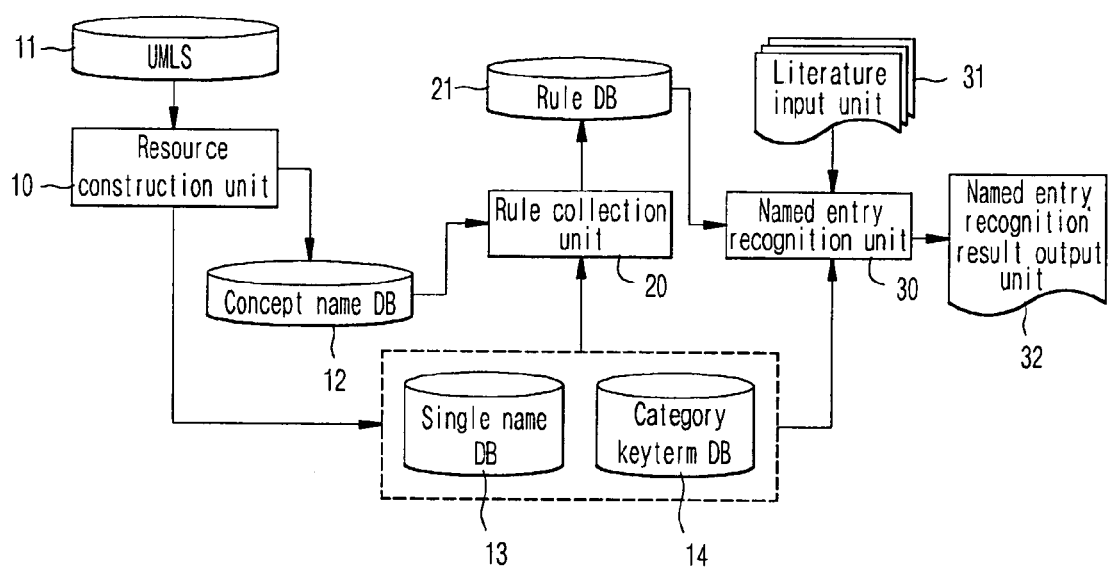
FIG. 1 illustrates entire configuration of an apparatus for recognizing biological named entity from biological literature based on UMLS (United Medical Language System) according to an embodiment of the present invention.

FIG. 1 illustrates entire configuration of an apparatus for recognizing biological named entity from biological literature based on UMLS according to an embodiment of the present invention.

As shown in FIG. 1, the apparatus for recognizing biological named entity according to an embodiment of the present invention includes a resource construction unit 10, a rule collection unit 20 and a named entity recognition unit 30. The resource construction unit 10 receives metathesaurus from the UMLS 11 and constructs a concept name database 12, a single name database 13 and a category keyterm database 14, which are language resources to be used to recognize named entities. The rule collection unit 20 receives each concept name stored in the concept name database 12, extracts a feature of each of the concept names by using data stored in the single name database and the category keyterm database, and constructs a rule database 21 by creating rules used to recognize the named entities and filtering the rule by using the extracted feature. The named entity recognition unit 30 receives a biological literature through the literature input unit 31, extracts nouns and noun phrases that are candidate named entities from the input literature, applies the rules stored in the rule database 21 to the nouns and the noun phrases, and recognizes the named entities.

Referring to FIGS. 2 to 10, description will be made on the apparatus and method for recognizing biological named entity from biological literature based on UMLS. The method for recognizing a biological named entity according to an embodiment of the present invention includes a resource construction step, a rule collection step and a named entity recognition step. Each step mentioned above will be described in detail referring to the drawings.

Figure 2:
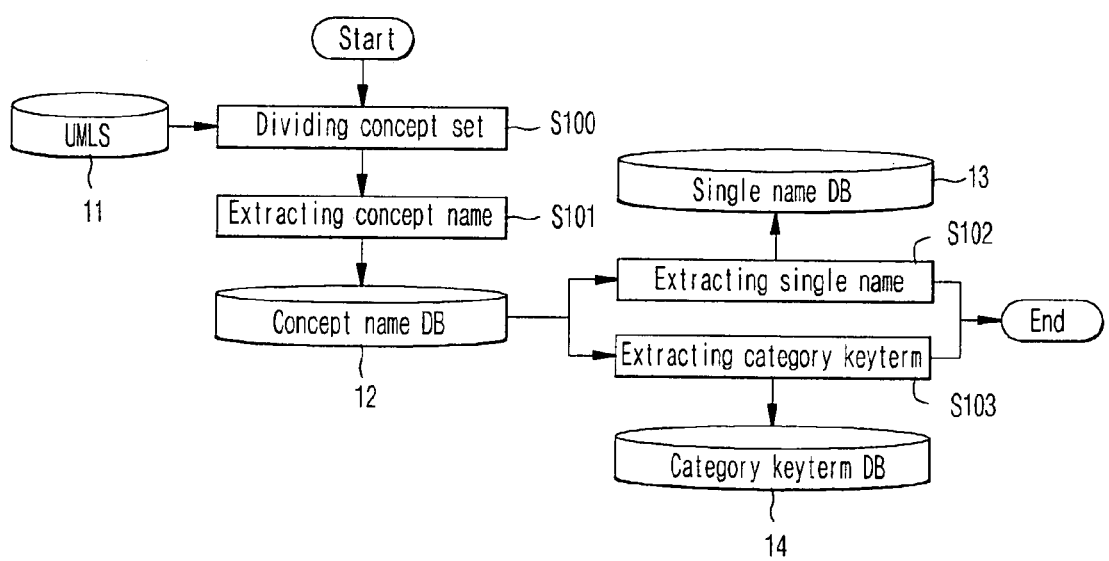
FIG. 2 illustrates a resource construction step in a method for recognizing biological named entity according to an embodiment of the present invention.

First, referring to FIG. 2, the resource construction step will be described. FIG. 2 illustrates a resource construction step in the method for recognizing biological named entity according to an embodiment of the present invention.

As described above, the resource construction unit 10 shown in FIG. 1 constructs a concept name database 12, a single name database 13 and a category keyterm database 14, which are language resources to be used to recognize a named entity. Metathesaurus supplied to the resource construction unit 10 from the UMLS includes information on concepts that appear at least once in various controlled vocabulary and classification used in a biomedical field.

When the resource construction step starts as shown in FIG. 2, a concept set division step is first performed (S100). In the concept set division step S100, among tables included in the metathesaurus of the UMLS 11, the information in MRCON table used to describe meaning of each string representing the concept name is mapped to the information in MRSTY table used to describe semantic categories allocated to each concept name by using a mapping condition shown in FIG. 3. Then, the data stored in the MRCON table is divided according to each semantic category. FIG. 3 illustrates a mapping relation between MRCON table and MRSTY table used to divide concept names according to semantic categories in a method for recognizing biological named entity according to an embodiment of the present invention. In the mapping condition shown in FIG. 3, if unique identifier for concept (CUI) of the MRCON table is identical to CUI of the MRSTY table, only data that the value of language of term (LAT) is "ENG", among the data in the MRCON table, is divided into sets different from one another according to a value corresponding to unique identifier of semantic type (TUI) of the MRSTY table.

Then, the concept name extraction step S101 is performed. In the concept name extraction step S101, the concept names that are values in a string (STR) field of the MRCON table are extracted from the result of the concept set division step S100 of dividing data in the MRCON table according to the semantic category, and stored in the concept name database 12.

Then, a single name extraction step S102 and a category keyterm extraction step S103 are performed. In the single name extraction step S102, the single names in which a single word itself is used as a named entity are extracted from the concept name database 12 and stored in the single name database 13. Since the single name can be used in various semantic categories, the information on semantic category in which the single names are used is stored together in the single name database 13. In the category keyterm extraction step S103, a category keyterm, which frequently appears in a specific category and is an important word in constituting named entity, is extracted from the concept name database 12 and stored in the category keyterm database 14. The category keyterm is obtained by calculating distribution ([appearance frequency of the most frequent appearance category]/[appearance frequency of all the category]) in the semantic category where each word constituting the named entity appears most frequently, and by filtering the words with a threshold. When a single name extraction step S102 and a category keyterm extraction step S103 are completed, the resource construction step is completed.

Next, referring to FIG. 4, the rule collection step will be described. FIG. 4 illustrates a rule collection step in a method for recognizing biological named entity according to an embodiment of the present invention.

The rule collection unit 20 of FIG. 1 receives each concept name stored in the concept name database 12, extracts a feature of a token, combines (constitutes) the extracted features in the form of the rule, and constructs a rule database 21. The rule collection step includes a feature extraction step S200 and a rule constitution step S201. The detailed configurations of the feature extraction step S200 and the rule constitution step S201 are illustrated in FIGS. 6 and 7.

When the rule collection step starts, the feature extraction step S200 is first performed. In the feature extraction step S200, the feature is extracted from each concept name according to a feature extraction flow shown in FIG. 6 by using various features which are shown in FIGS. 5A to 5F and defined to reflect properties of a biological named entity. Since the biological named entities usually include capital letter expression, numbers, and characters other than alphabets, the features such as capital letter expression, alphanumeric and special character shown in FIG. 5A are used. Since the biological named entity may include preposition or conjunction, and may include a word representing a function or category of an individual, the feature of preposition or conjunction and the features of single name and category keyterm are used respectively as shown in FIG. 5A. In order to represent the case that a named entity token does not belong to any of the features, the feature "miscellaneous" shown in FIG. 5A is used. Each feature has subtypes. The features of the single name and category keyterm have semantic categories defined to recognize a named entity as there own subtypes. The features of capital letter expression, alphanumeric, preposition and conjunction, special character and miscellanies have subtypes as shown in FIGS. 5B to 5F.

Figure 6:
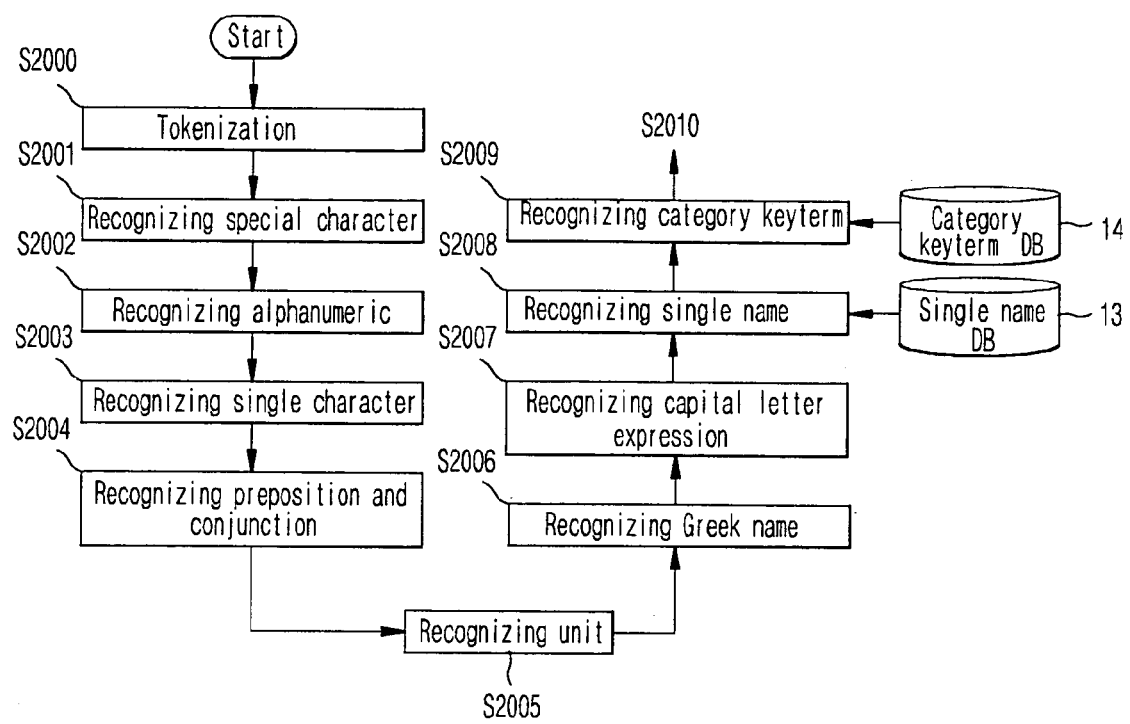
FIG. 6 is a more detailed flowchart illustrating feature extraction step shown in FIG. 4.
Figure 7:
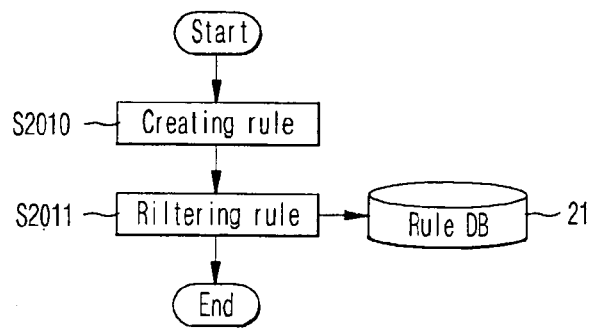
FIG. 7 is a more detailed flowchart illustrating rule constitution step shown in FIG. 4.

The feature extraction step S200 shown in FIG. 4 is illustrated in FIG. 6 in detail. The feature extraction step S200 is used in the cases shown in FIGS. 4 and 10 respectively, and is used by the rule collection unit 20 and the named entity recognition unit 30 to receive the concept name and the candidate named entity to extract features of each of tokens constituting the concept name and the candidate named entity respectively. Referring to FIG. 6, the feature extraction step S200 will be described in detail. When the feature extraction step S200 starts, a tokenization step S2000 is performed. In the tokenization step S2000, the concept names stored in the concept name database 12 and the candidate named entities extracted from the literature input unit 31 are divided into tokens by using a space letter and special characters. The tokens divided at the step S2000 experience a special character recognition step S2001, an alphanumeric recognition step S2002, a single character recognition step S2003, a preposition and conjunction recognition step S2004, a unit recognition step S2005, a Greek name recognition step S2006, a capital letter expression recognition step S2007, a single name recognition step S2008 and a category keyterm recognition step S2009 sequentially so that the features shown in FIGS. 5A to 5F are extracted at the corresponding steps. In the single name recognition step S2008 and the category keyterm recognition step S2009, it is checked whether a token exists in the single name database 13 and the category keyterm database 14 constructed by the resource construction unit 10, and the subtypes of the corresponding single name and the category keyterm are obtained. When the category keyterm recognition step S2009 is completed, the feature extraction step s200 is completed. It goes to the rule creation step S2010 so that the detailed steps of the rule constitution step S201 shown in FIG. 4 is performed.

The rule constitution step S201 includes a rule creation step S2010 and a rule filtering step S2011. In the rule constitution step S201, the feature obtained at the feature extraction step S200 in which the concept name is tokenized and the feature is extracted as shown in FIG. 4 is inputted, and the rule to recognize the named entity is created and filtered to finally construct the rule database 21.

Figures 8, 9:
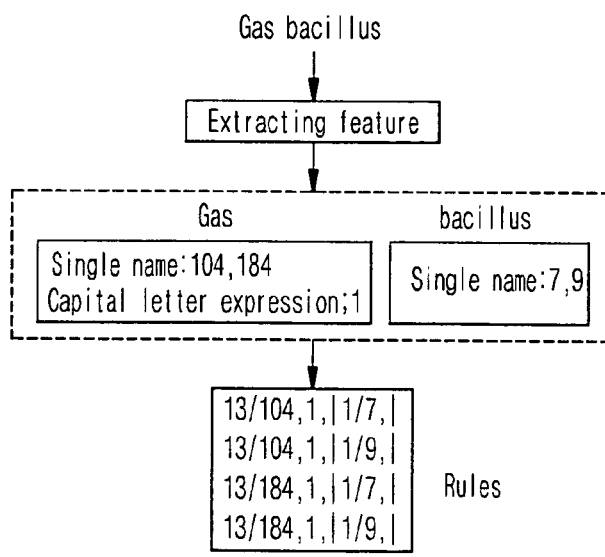
FIG. 8 is an example of expression of a rule used in a method for recognizing biological named entity according to an embodiment of the present invention.
FIG. 9 is an example of constitution of a rule for a specific concept name in a method for recognizing biological named entity according to an embodiment of the present invention.

Referring to FIG. 7, in the rule creation step S2010, the tokens of the concept names are combined to constitute the rule used to recognize the named entity as a rule expression manner shown in FIG. 8. Here, if the token has a feature of a single name, one single name can have various subtypes so that the rule in which such subtypes are all considered should be created. FIG. 9 is an example of constitution of a rule for a specific concept name "Gas bacillus". The concept name "Gas bacillus" can be divided into two tokens "Gas" and "bacillus". When features are extracted from each token, "gas " has the feature of a capital letter and the feature of a single name, and "bacillus" has only the feature of a single name. Since each of the features of the single names of "gas " and "bacillus" has two subtypes, four rules are created considering all the combinations of them as shown in FIG. 9. In the rule filtering step S2011 of FIG. 7, [rule appearance frequency in a specific category]/[rule appearance frequency in all the categories] is calculated for all the rules created in the rule creation step S2010 and the rules are filtered with a threshold to construct the rule database 21. When the rule filtering step S2011 is completed, the rule constitution step S201 is completed.

Figure 10:
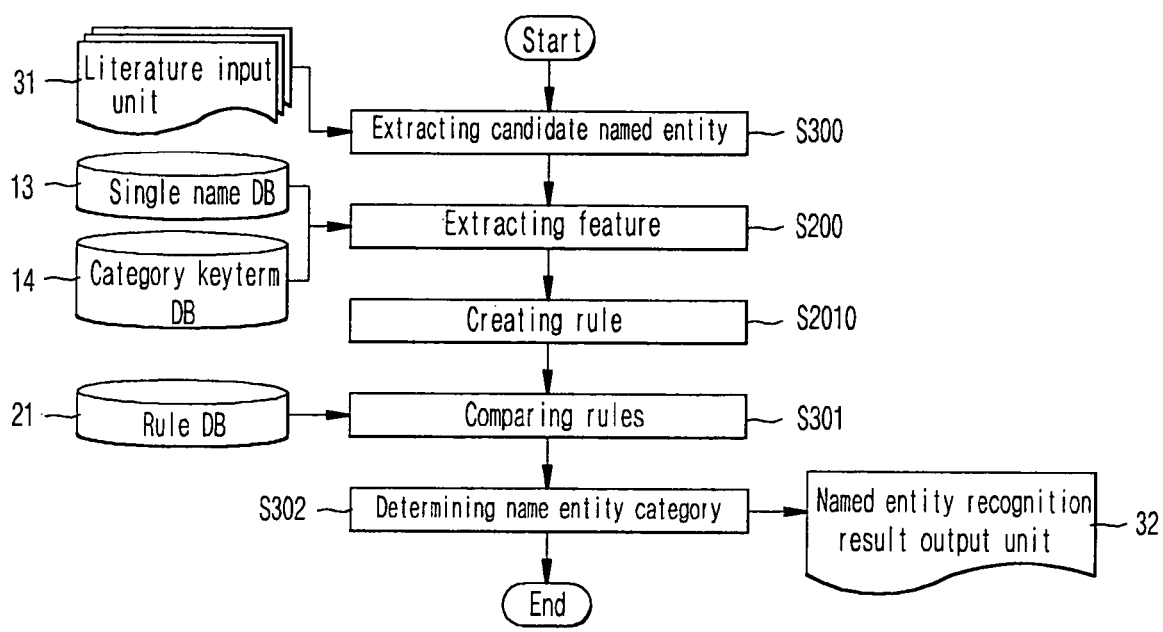
FIG. 10 illustrates a named entity recognition step in a method for recognizing biological named entity according to an embodiment of the present invention.

As described above, when the rule constitution step S201 is completed, the named entity recognition step is performed by the named entity recognition unit 30. FIG. 10 illustrates a named entity recognition step in detail. The named entity recognition unit 30 applies the rule stored in the rule database 21 to the literature supplied from the literature input unit 31 to recognize the named entity. Referring to FIG. 10, the named entity step will be described in detail.

Referring to FIG. 10, when the named entity recognition step starts, a candidate named entity extraction step S300 is first performed. In the candidate named entity extraction step S300, a morpheme parsing is performed on the literature supplied from the literature input unit 31, and nouns and noun phrases, which are candidate named entities, are extracted from the input literature. Here, the noun phrase does not mean only the phrase consisting simply of consecutive nouns but means the phrase consisting of articles, prepositions, conjunctions and nouns. When the named entity extraction step S300 is completed, the feature extraction step S200 is performed. In the feature extraction step S200, the feature is extracted from the noun and the noun phrase obtained in the named entity extraction step S300. Here, in the feature extraction step S200, the features are extracted from the single name and the category keyterm by using information stored in the single name database 13 and the category keyterm database 14 constructed by the resource construction unit 10 shown in FIG. 1. Next, in the rule creation step S2010, the tokens obtained by applying the feature extraction step S200 to the candidate named entity are combined in a rule expression manner shown in FIG. 8, thereby creating the rule.

Then, in rule comparison step S301, the rule of the candidate named entity, which was created at the rule creation step S2010, is compared with the rules stored in the rule database 21 in manners of exact match, partial match and nested match to extract the existing rules suitable for the candidate named entity. The exact match means that both rules match each other exactly. The partial match means that both rules match each other in their front portion, middle portion or rear portion. The nested match means that one rule include another matched rule.

Next, the named entity category determination step S302 is performed. In the step S302, the final semantic category of the candidate named entity is determined using a weight value of the existing rules extracted at the rule comparison step S301 and a few heuristics used to determine a category of the named entity, and transferred to the named entity recognition result output unit 32. The named entity recognition result output unit 32 provides the recognition result of the biological named entity.

The method for recognizing the biological named entity from the biological literature based on UMLS according to an embodiment of the present invention is made into a computer program and can be stored in a storage medium such as a hard-disc, a floppy disc, a magneto-optical disc, a CD-ROM, ROM, RAM, etc.

As described above, in an apparatus and method for recognizing biological named entity from biological literature based on UMLS according to the present invention, biological language resources are automatically constructed, and named entity used in biological literature is automatically recognized using the automatically constructed biological language resources so that efforts and costs can be saved in constructing a biological named entity recognition system. Furthermore, the biological named entity recognizer can be quickly configured regardless of domains without any aid of experts so that information extraction from biological literature can be more actively studied.

The above description is merely an embodiment of the apparatus and method for recognizing biological named entity from biological literature based on UMLS according to the present invention. It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A method for recognizing a biological named entity from biological literature based on United Medical Language System (UMLS), the method comprising the steps of:
   (a) receiving metathesaurus from the UMLS;
   (b) extracting concept names, single names and category keyterms;
   (c) constructing a concept name database, a single name database and a category keyterm database;
   (d) constructing a database of rules based upon information stored within the concept name database, the single name database, and the category keyterm database;
   (e) inputting a literature;
   (f) extracting candidate named entities from the literature; and
   (g) recognizing named entities from the candidate named entities based upon the rules applied against the single name and category keyterm databases,
   wherein the step (b) comprises the steps of:
   (b-1) mapping information in MRCON table used to describe meaning of each string representing the concept name to information in MRSTY table used to describe a semantic category allocated to each concept name among tables included in the metathesaurus by using a mapping condition, and dividing data stored in the MRCON table according to each semantic category;
   (b-2) extracting values in a string (STR) field of the MRCON table from result of dividing a concept set and storing the extracted values in the concept name database;
   (b-3) extracting single names from the concept name database and storing the extracted single names in the single name database; and
   (b-4) extracting category keyterms from the concept name database and storing the extracted category keyterm in the category keyterms database.

2. The method of claim 1, wherein in the mapping condition for mapping information in the MRCON table and the MRSTY table, if unique identifier for concept (CUI) of the MRCON table is identical to CUI of the MRSTY table, only data that the value of a language of term (LAT) field is "ENG" among the data in the MRCON table are divided into different sets from one another according to a value corresponding to unique identifier of semantic type (TUI) of the MRSTY table.

3. The method of claim 1, wherein the step (b-4) comprises the steps of:
   calculating distribution in the semantic category where each word constituting the named entity appears most frequently by using the concept names stored in the concept name database;
   and filtering the words with a threshold.

4. The method of claim 1, wherein the step (d) comprises the steps of:
   (d-1) extracting the features from each of the concept names stored in the concept name database according to a token; and
   (d-2) generating the rule by combining the tokens whose features are extracted, calculating weight value of the constituted rule, filtering the rules with their weight values, and storing the filtered rules in the rule database.

5. The method of claim 4, wherein in the step (d-1), the feature of the tokens of each of the concept names stored in the concept name database is extracted using the features of the category keyterm, the single name and a capital letter expression, an alphanumeric, a special character, a preposition or conjunction, which are features defined to reflect characteristics of the biological named entity, and a subtype of each of the features.

6. The method of claim 4, wherein the step (d-2) comprises the steps of:
   receiving the result in which the concept name is tokenized and the features are extracted at the step (d-1), and creating the rules as many as the number of combinations of subtypes according to the subtypes of the features of the token; and
   calculating appearance distribution of the rule in each category on all the created rules, filtering the rules with the threshold, and constructing the rule database.

7. The method of claim 1, wherein the steps (f) and (g) comprises the steps of:
   (f-1) extracting nouns and noun phrases, which are candidate named entities, from the inputted literature;

(g-1) extracting features of each token of a candidate named entity;

(g-2) combining the features extracted from each of the tokens of the candidate named entity, and creating the rule used to determine the candidate named entity;

(g-3) comparing the created rule with the rules stored in the rule database; and (g-4) determining the final semantic category of the candidate named entity.

8. The method of claim 7, wherein in the step (g-3), existing rules suitable to determine the candidate named entity are extracted an existing rule by comparing the rule used to determine the candidate named entity with the rules stored in the rule database in manners of exact match, partial match and nested match.

9. The method of claim 7, wherein in the step (g-4), the final semantic category of the candidate named entity is determined using weight values of existing rules extracted at the step (g-3) and a heuristic used to determine a category of the named entity, and outputted as a result of recognizing the named entity.

\* \* \* \* \*